US005409835A

United States Patent [19]

Lakowicz et al.

[11] Patent Number: 5,409,835

[45] Date of Patent: Apr. 25, 1995

[54] LONG-WAVELENGTH FLUORESCENT PROBE COMPOUNDS FOR CALCIUM IONS AND THEIR USE IN RATIOMETRICALLY MEASURING CALCIUM ION CONCENTRATIONS

[75] Inventors: Joseph R. Lakowicz, Ellicott City; Engin U. Akkaya, Columbia, both of Md.

[73] Assignee: The University of Maryland at Baltimore, Baltimore, Md.

[21] Appl. No.: 998,849

[22] Filed: Dec. 30, 1992

[51] Int. Cl.[6] .................... G01N 33/52; C07D 277/62; C07D 277/70; C07D 335/04

[52] U.S. Cl. .................... 436/79; 436/63; 436/172; 436/800; 546/170; 548/148; 548/150; 548/180; 549/23

[58] Field of Search .................... 436/63, 79, 172, 800; 544/92, 105; 546/121, 170; 548/148, 149, 150, 180; 549/23

[56] References Cited

U.S. PATENT DOCUMENTS

| | | | |
|---|---|---|---|
| 3,660,102 | 5/1972 | Riester | 430/578 |
| 4,603,209 | 7/1986 | Tsien et al. | 548/236 |
| 4,689,432 | 8/1987 | Tsien et al. | 562/435 |
| 4,795,712 | 1/1989 | Toner et al. | 436/74 |
| 4,806,604 | 2/1989 | Tsien et al. | 549/439 |
| 4,849,362 | 7/1989 | DeMarinis et al. | 436/63 |
| 5,049,673 | 9/1991 | Tsien et al. | 546/107 |
| 5,085,946 | 2/1992 | Saito et al. | 428/690 |
| 5,094,958 | 3/1992 | Klainer et al. | 436/172 |
| 5,112,960 | 5/1992 | Bronstein et al. | 536/18.1 |
| 5,141,627 | 8/1992 | Tsien et al. | 204/157.88 |
| 5,212,307 | 5/1993 | Wilczak | 544/194 |
| 5,227,308 | 7/1993 | Jameson et al. | 436/172 |

OTHER PUBLICATIONS

Gurney, A. M. "Photolabile calcium buffers to selectively activate calcium-dependent processes" *Cell. Neuvobiology*, 153–77, 1991.

Deng et al. "Synthesis of a new fluorometric calcium ion indicator fura-3 and study on its properties." *Huaxne Shiji*, 14(1), 40–5, 1992.

Tsien et al. "Control of cytoplasmic calcium with photolabile tetracarboxylate 2-nitrobenzhydrol chelators". *Biophysics Journal*–50 (5), 843–5, 1986.

Lanza et al. "Increased aggregation and secretion responses of human platelets when loaded . . ." *Thromb. Haemostatis, 58 (2), 737–43 1987.*

Pethig et al. "On the dissociation constants of BAPTA-type calcium buffers" *Cell Calcium*, 10 (7), 491–8, 1989.

Zucker, R. S. "Effects of photolabile calcium chelators on fluorescent calcium indicators". *Cell Calcium*, 13 (1), 29–40, 1992.

Dubinsky, J. M. "Effects of calcium chelators on intracellular calcium and excitotoxicity" *Neurosci. Lett., 150 (2), 129–32, 1993.*

*Primary Examiner*—Robert J. Warden
*Assistant Examiner*—Robert Carpenter
*Attorney, Agent, or Firm*—Sughrue, Mion, Zinn, Macpeak & Seas

[57] ABSTRACT

Fluorescent, calcium-binding probe compounds having visible-light excitation and emission wavelengths, and a method of usage for these probe compounds in making wavelength-ratiometric or intensity-ratiometric measurements of calcium ion concentration in samples. The probe compounds generally relate to a heterocyclic part as bonded to a $Ca^{2+}$ binding unit, namely, BAPTA, via an ethylenically unsaturated group; preferred examples of the heterocyclic group include benzothiazole, naphthothiazole, thiaflavin, indolenine, chloroindolenine, methoxybenzothiazole, and methoxyindolenine.

18 Claims, 5 Drawing Sheets

CH3OOC COOCH3 CH3OOC COOCH3 N N O O CHO CH3 1
1M NaOH (aq) reflux
HOOC COOH HOOC COOH N N O O CHO CH3 2
S CH3 N C2H5 3
Et3N, EtOH
⊖OOC COO⊖ ⊖OOC COO⊖ N N O O CH3 C H H C S N⊕ — C2H5
4 (STBT)

LONG-WAVELENGTH FLUORESCENT PROBE COMPOUNDS FOR CALCIUM IONS AND THEIR USE IN RATIOMETRICALLY MEASURING CALCIUM ION CONCENTRATIONS

ACKNOWLEDGEMENT

This invention was made in part with government support from the National Institutes of Health and the NSF.

BACKGROUND OF THE INVENTION

1. Field of the Invention

The present invention relates to a new class of fluorescent, calcium-binding probe compounds having visible-light excitation and emission wavelengths, and to the use of these probe compounds for making wavelength-ratiometric or intensity-ratiometric measurements of calcium ion concentrations in samples. The invention is particulary well-suited for making wavelength-ratiometric or intensity-ratiometric measurements of intracellular $Ca^{2+}$ levels in which the $Ca^{2+}$ measurements can be accomplished independent of the overall concentration of the probe compound.

2. Description of the Related Art

Calcium is a recognized intracellular messenger and mediator. Consequently, it is not surprising that many and varied proposals for measuring calcium ion concentrations have been proposed in the field for the purpose of facilitating the study of cell activity, such as cell response to a variety of stimuli.

To achieve this purpose, most proposals for measurements of intracellular $Ca^{2+}$ use fluorescence indicators, such as Quin-2, Indo-1 and Fura-2, as described for example in U.S. Pat. No. 4,603,209 and Soc. Gen. Physiol. Ser., V. 40, 1986, pages 327–45.

However, it is difficult to design novel fluorophores which are both specific for calcium and which display fluorescence spectral shifts upon calcium binding. In fact, only a small fraction of the known chromophores display satisfactory fluorescent properties and chemical specificity in an aqueous solution.

Therefore, in spite of the past intense efforts to acquire suitable calcium ion probes, these efforts have been disappointing because of the severe limitations encountered with the heretofore proposed dyes.

For instance, the known dyes, such as Quin-2, require excitation in the UV wavelength range where autofluorescence from cells is excited. Further, the transmission of UV light in microscopic optics applications is deficient, as explained in U.S. Pat. No. 4,603,209. For example, microscope optics are traditionally corrected for chromatic aberration in the visible region of the spectrum. This creates problems in the area of confocal microscopy, which requires precise alignment of pinhole apertures for a range of excitation wavelengths.

In the case of existing wavelength-ratiometric calcium probes, these wavelengths are in the UV region, and the confocal measurements also fail because of uncorrected chromatic aberration in this wavelength region. Additionally, there are simpler and less expensive laser sources available for visible wavelengths rather than for UV wavelengths, which enable not only disc scanning confocal microscopy, but also laser scanning confocal microscopy.

Moreover, other known dyes, such as Fura-2 and Quin-2, are subject to photobleaching, and, perhaps, even more important, photoconversion to $Ca^{2+}$-insensitive forms. These insensitive dye forms are fluorescent and interfere with the determination of the $Ca^{2+}$ concentration, as described in U.S. Pat. No. 5,049,673.

Therefore, because of these troublesome problems associated with the UV-excited dyes, there has been recognized a need for $Ca^{2+}$ probes having improved photostability and longer wavelength absorption and emission. That is, longer wavelength absorption is desirable because the amount of autofluorescence decreases progressively as a function of increasingly longer wavelengths for excitation of the probe.

There exist in the prior art several proposals for satisfying this need. For instance, U.S. Pat. No. 4,849,362 describes longer wavelength tetracarboxylate compound chelators for calcium ions. The tetracarboxylate compounds in U.S. Pat. No. 4,849,362 are reported to experience an increase in fluorescence intensity upon excitation, and the optical responses reportedly could be determined by using a single visible wavelength laser line for excitation. However, the probes in U.S. Pat. No. 4,849,362 do not display any spectral shifts upon calcium binding and thus wavelength-ratiometric measurements are not possible with the dyes described in this patent.

That is, the field has not only appreciated the need to provide a longer-wavelength (visible light) fluorescent dye for making calcium ion measurements, but also has further envisaged the possible salutary benefits that could be obtained by the discovery of a fluorescent dye capable of enabling wavelength-ratiometric measurements of $Ca^{2+}$ concentrations.

As understood in the field, the phrase "wavelength-ratiometric measurement" generally means a ratio of intensities measured at two different excitation or emission wavelengths. That is, a "wavelength-ratiometric measurement" means making a calcium concentration measurement in a sample by a process wherein the calcium ion-containing sample is excited at two different wavelengths, sequentially, and the resulting fluorescence intensities are measured for each excitation, and the ratio of the respective fluorescence intensities provides an indication of the calcium ion concentration in the sample when compared to a calibration curve.

This ratiometric measuring ability in a dye is highly desirable and often necessary because the probe concentration cannot be easily controlled (and/or the emitted fluorescence cannot be controlled) in flow cytometry, microscopy, or in cuvette studies involving cell suspensions.

The acute difficulties in developing a long-wavelength fluorescent dye which is concomitantly capable of providing such ratiometric measurements of calcium ions in intracellular samples is highlighted in recent U.S. Pat. No. 5,049,673 which proposes certain visible-wavelength fluorescent dyes of a RHOD series and a FLUO series.

However, the elusiveness of developing such long-wavelength probes that also permit ratiometric measurements is recognized in the U.S. Pat. No. 5,049,673. In this regard, U.S. Pat. No. 5,049,673 reports the inability to provide long-wavelength fluorophores which have wavelength pairs in either excitation or emission that are suitable and needed for fluorescence ratioing.

As stated in U.S. Pat. No. 5,049,673, ratioing would be extremely valuable with single cells because it cancels out variations in dye concentration and path length. Without such ratioing, it is impossible to correlate dye fluorescence intensity with $Ca^{2+}$ levels in a simplified manner.

U.S. Pat. No. 5,049,673 concedes that the proposed dyes disclosed therein had only small or negligible shift in absorbance, excitation or emission wavelengths upon $Ca^{2+}$ binding; consequently, such dyes of that patent are unsuitable for accomplishing fluorescence ratioing.

However, from a more general perspective, certain derivatives of BAPTA have been proposed as absorption and/or colorimetric indicators which are reported to be detectable at longer wavelengths which would shift to other wavelengths when complexed with calcium. This shifting would allow quantitative analysis for calcium without interference from UV and short-wavelength visible light-absorbing species, such as disclosed in U.S. Pat. No. 4,795,712.

However, U.S. Pat. No. 4,795,712 does not describe the ability of the dyes described therein to fluoresce, much less the application of such dyes to fluorescence detection. Instead, U.S. Pat. No. 4,795,712 is directed only to the use of certain chelating compounds to detect $Ca^{2+}$ in liquids or spread (dry) samples based on changes in the visible absorbance and/or reflective spectra of samples containing these compounds.

In any event, U.S. Pat. No. 4,795,712 does not address the development of fluorescent dye compounds capable of permitting ratiometric measurements of calcium ions in intracellular environments using fluorescence detection.

Further, in general, it is known that the BAPTA chelating group is valuable in cellular systems because of its specificity for $Ca^{2+}$ and low affinity for $Mg^{2+}$, $Na^{+}$ or $K^{+}$ (R. Y. Tsien, *Methods in Cell Biology,* 1989, Academic Press, London; R. Y. Tsien, *Biochem.,* 1980, 19: 2396–2404).

Another desirable feature of potential probes is the use of charge steering by cations, which are described heretofore using crown ether and azacrown moieties (H. G. Löhr and F. Vögtle, 1985, *Acc. Chem. Res.,* 1985, 18: 65–72). According to the above-described prior art, there have been synthesized various probes which contain such substances as styryl dyes, various chromophores, and crown ethers to complex cations. These types of substances can display changes in their absorption spectra in response to cation binding. For example, see J. F. Alder, D. C. Ashworth, R. Narayanaswamy, R. E. Moss and I. O. Southerland, 1987, *Analyst,* 112: 1191–1192; S. Fery-Forgues, M. T. LeBris, J. P. Guette and B. Valeur, *J. Chem. Soc.,* Chem. Commun. 1988, 385; J. Bourson and B. Valeur, *J. Phys. Chem.,* 1989, 93: 3871–3876; S. Fery-Forgues, M. T. LeBris, J. P. Guette and B. Valeur, *J. Phys. Chem.,* 1988, 92: 6233–6237; M. V. Alfimov, S. P. Gromov and I. K. Lednev, 1991, *Chem. Phys. Lett.,* 185: 455–460.

However, these prior usages of crown ether chemistry resulted in low specificity and/or affinity for $Ca^{2+}$, which effectively precludes the use of these probes in cellular systems. Additionally, these prior crown ether probes did not contain carboxylic acid groups or provide the opportunity for cell labeling via the acetoxymethylester-esterase trapping procedure. Also, the use of simpler fluorophores did not result in fluorescence spectral shifts (K. W. Street, Jr., *Anal. Lett.,* 1986, 19: 735–745).

In view of the above-discussed technological backdrop, it is apparent that the field has urgently awaited the innovative development of long-wavelength fluorescent compounds which are concomitantly able to permit wavelength-ratiometric or intensity-ratiometric measurements of $Ca^{2+}$ concentrations, especially intracellular calcium concentrations.

SUMMARY OF THE INVENTION

The problems noted above are overcome by the long-wavelength fluorescent calcium-binding probe compounds of the present invention which have the following general structure:

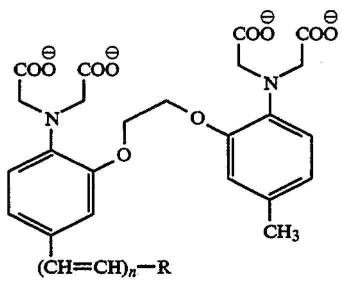

wherein n represents an integer of 1, 2 or 3 and R represents a substituted or unsubstituted unsaturated heterocyclic group.

The heterocyclic group can be a 5- to 6-membered ring (single or fused ring), wherein the hetero atoms can be selected from oxygen, nitrogen, sulfur, selenium or tellurium, and the like. Further, as will become more apparent from examples provided hereinafter, multiple hetero atoms can be provided in the heterocyclic ring.

In a one preferred embodiment of the present invention, the heterocyclic group R represents a heterocyclic group selected from the group consisting of benzothiazole, quinaldine, thiaflavin, thiapyran, quinoline and benzoxazinone derivatives. The use of benzothiazole as the heterocyclic group is particularly preferred.

In another embodiment of the present invention, a method of making wavelength-ratiometric or intensity-ratiometric measurements of the calcium concentration in a sample, especially intracellular $Ca^{2+}$, comprises contacting the sample with the compounds described above in sufficient quantity to act as a fluorescent optical indicator independent of the concentration of the probe compound.

This wavelength-ratiometric or intensity-ratiometric measurement of calcium concentration is adaptable to fluorescence microscopy and flow cytometry, as well as to standard spectrophotometry.

That is, in one embodiment for making calcium concentration measurements in the present invention, the inventive probe compound can be used as a wavelength-ratiometric probe wherein the calcium ion-containing sample is excited at two different visible wavelengths, sequentially, and the resulting fluorescence intensities are measured for each excitation, and the ratio of the respective fluorescence intensities can be processed to provide an indication of the calcium ion concentration in the sample from a calibration curve.

Importantly, this ratiometric measurement of the calcium level in the sample is accomplished independent of the concentration of the probe compound in the sample.

The term, ratiometric, as used herein, refers to the ability to make measurements of the $Ca^{2+}$ level in a sample which are independent of the overall probe or dye concentration. Also, the recognized wavelength band for visible wavelengths is about 400 nm to about 670 nm. This visible wavelength band is, at times, used herein interchangeably with the term long wavelength.

As another embodiment for making calcium concentration measurements in the present invention, the inventive probe compound may even be used as an emission wavelength probe wherein the calcium ion-containing sample is excited at a single excitation wavelength and observed at two emission wavelengths.

In this embodiment, the fluorescence intensity of the probe compound is measured by illumination with a single visible excitation wavelength and the emission intensity is measured at two emission wavelengths. The level of calcium ions in the sample is correlated to and can be determined from the ratio of these two measured emission intensities.

However, the ability to practice this embodiment of the present invention depends on whether the particular probe compound fluoresces in the absence of calcium, which is either a known attribute or can be readily determined for the probes of interest within the scope of the present invention. Further, in this embodiment, in addition to fluorescence in the absence of calcium, the probe must also display a different emmission spectrum in the presence and absence of calcium.

The emission spectra display modest shifts upon binding to the probe compounds of the present invention. Also, upon $Ca^{2+}$ binding in the probe compounds of the present invention, the absorption spectrum shifts dramatically to shorter wavelengths upon complexation with $Ca^{2+}$. Generally, the emission wavelengths for the probes of the invention fall into the visible wavelength band.

For instance, the visible absorption spectrum of the probes of the present invention display a dramatic shift in the long wavelength maxima from 508 nm to 407 nm upon complexation with $Ca^{2+}$, with a $Ca^{2+}$ dissociation constant of 1.5μM. The emission maximum centered at 615 nm is well shifted from the absorption. Further, the emission spectrum displays a small blue shift upon binding $Ca^{2+}$. This feature is significant because it allows those probes of the present invention to be used as a emission wavelength ratiometric probe using a single excitation wavelength.

Therefore, the inventive probe compounds of the present invention successfully combine the use of a BAPTA chelating group and a charge-sensitive dye, such as styryl dyes.

As will be appreciated the fluorescent probe compounds and their method of usage in this present invention represent a significant advance in the field.

Namely, the probe compounds of the present invention can be used in long-wavelength or visible light regions to thereby avoid the autofluorescence and other mentioned problems associated with the use of UV excitation wavelengths. Concomitantly, the fluorescent probe compounds of the present invention enable wavelength-ratiometric or intensity, ratiometric measurements to be performed on calcium ion-containing samples, i.e., measurements independent of the overall probe concentration.

DETAILED DESCRIPTION OF THE INVENTION

Figure 1:
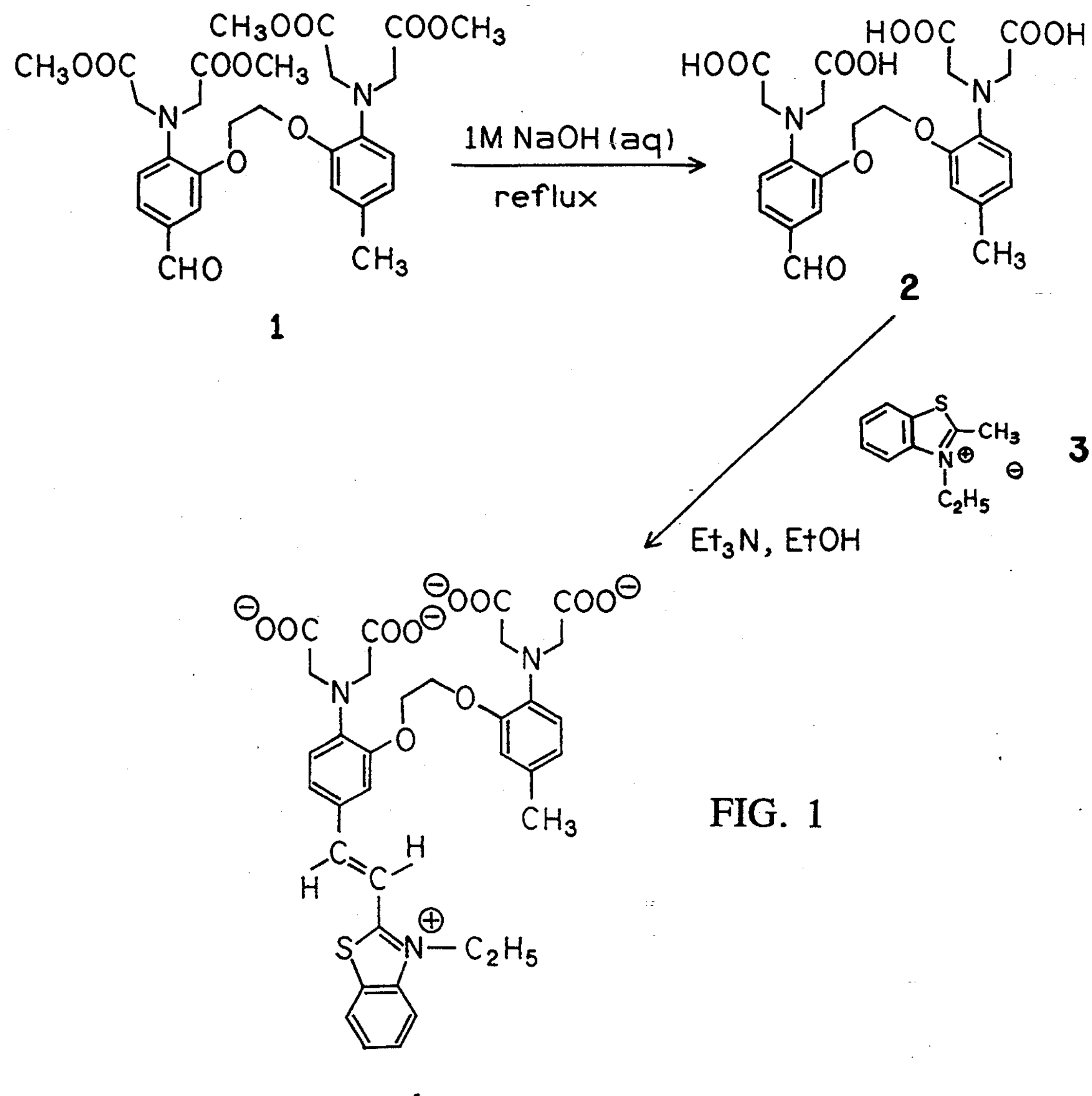
FIG. 1 shows an exemplary synthetic pathway leading to an exemplary calcium binding styryl benzothiazole (STBT) $Ca^{2+}$ probe compound of the present invention.

The present invention represents a new class of fluorescent calcium-binding indicator compounds which are excitable by visible-wavelength light and which enable wavelength-ratiometric or intensity-ratiometric measurements of $Ca^{2+}$ levels. The probe compounds of the present invention generally relate to a heterocyclic part as bonded to a $Ca^{2+}$ binding unit via an ethylenically unsaturated group. For purposes of the present invention, the $Ca^{2+}$ binding unit is 1,2-bis-(2-aminophenoxy)ethane -N,N,N′,N′-tetraacetic acid, which is commonly referred to as BAPTA.

For purposes of the present invention, the BAPTA encompasses substituted derivatives of BAPTA which retain the essential characteristics of the BAPTA. This definition encompasses the possible conversion of carboxylates to cell-permeable acetoxy methyl (AM) esters.

Preferred examples of the heterocyclic group include benzothiazole, quinaldine, thiaflavin, thiapyran, quinoline and benzoxazinone derivatives. Representative chemical structures of suitable heterocyclic groups, designated as R-1 to R-14, are illustrated below, wherein X can be methyl, ethyl, sulfopropyl, sulfobutyl and carboxymethyl:

R-1

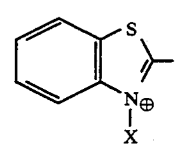

R-2

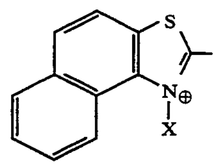

R-3

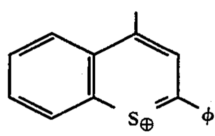

-continued

R-4

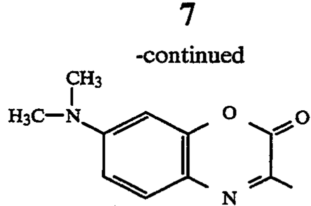

R-5

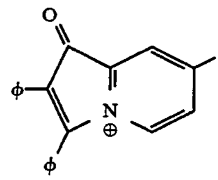

R-6

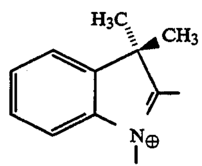

R-7

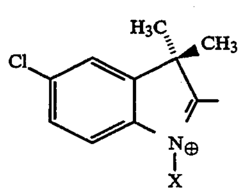

R-8

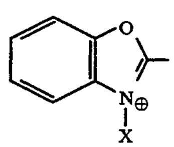

R-9

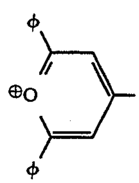

R-10

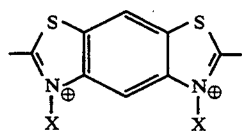

R-11

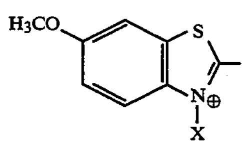

R-12

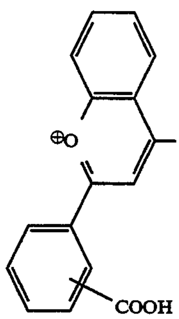

-continued

R-13

R-14

Of the above chemical structures, R-1 is benzothiazole, R-2 is naphothiazole, R-3 is thiaflavin, R-6 is indolenine, R-7 is chloroindolenine, R-11 is methoxybenzothiazole, and R-13 is methoxyindolenine.

As mentioned above, the heterocyclic group is linked to the calcium ion chelating group, namely BAPTA, via an ethylenically unsaturated group. This ethylenically unsaturated group can be a vinyl or conjugated-double bond containing group. The conjugated chain length can be increased by an ethylene unit(s) to shift absorption/emission by approximately 100 nm per unit.

The conjugated double bond also can be provided in a hardened or rigid cyclic structure, such as illustrated below in exemplary dye structures C-1 to C-5:

C-1

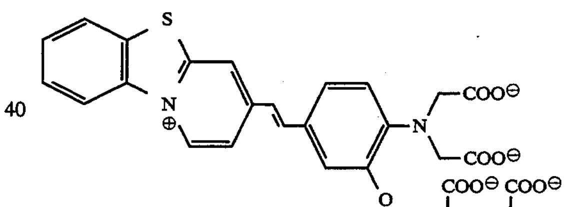

C-2

-continued

C-3

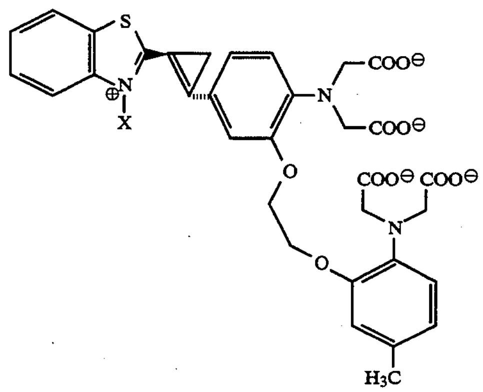

C-4

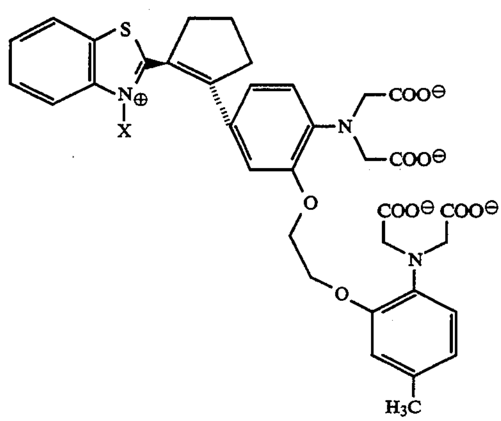

C-5

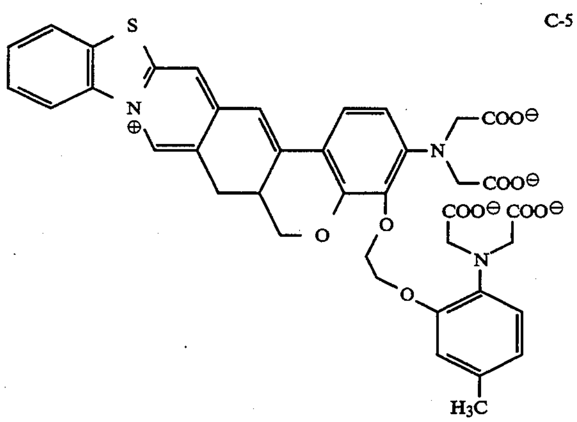

The discussion hereinafter provides a general overview of an exemplary manner for making calcium concentration measurements of the present invention, wherein the inventive probe compound is used as a wavelength ratiometric probe. This measurement can be accomplished with conventional equipment, such as described herein. The necessary support equipment arrangements needed to make the wavelength ratiometric measurements of the present invention are generally known. However, the present invention more concerns the discovery of particular long wavelength $Ca^{2+}$ probe or dye compounds which actually enable ratiometric measurements to be achieved and at visible wavelengths.

For example, the light source used to illuminate the calcium sample containing the probe compound of the present invention preferably is one capable of generating different wavelengths of light. The light source is effectively filtered through a conventional dispersive element and multiplexer to select the excitation wavelengths.

When the probe compound of the present invention is used as a excitation wavelength-ratiometric probe, the $Ca^{2+}$-containing sample is sequentially illuminated with two different excitation wavelengths $\lambda_1$ and $\lambda_2$ at two different time intervals $t_1$ and $t_2$, respectively. When the light illuminates the sample, a fluorescence is emitted as radiation from the $Ca^{2+}$-complexed probe compound for each of the two different excitation wavelengths.

This radiation, in turn, is captured by an optics subsystem and focused onto a video camera or other imaging detector, which can be selected from known equipment. In particular, the fluorescence intensity of the sample is monitored by the video camera at the same wavelength for each of the two different excitation wavelengths as $I_1$ and $I_2$. Each of the two light intensity signals are converted into electric signals such as output voltages.

The intensities can be measured at single points, to provide a single calcium concentration, or measured as two-dimensional arrays in which case, calcium concentration images are obtained.

In turn, these two electric signals are directed to a signal processing system, such as a microprocessor, where the ratio of the two electric signals derived from intensities $I_1$ and $I_2$ provides an indication of the calcium concentration from a predetermined calibration curve.

This ratiometric measurement of the calcium level in the sample is accomplished independent of the concentration of the probe compound in the sample.

A discussion is provided below on the other embodiment for making calcium concentration measurements in the present invention wherein the inventive probe compound can be used as an emission wavelength probe.

That is, in this embodiment, the calcium ion-containing sample is excited at a single excitation wavelength and observed at two emission wavelengths. In this embodiment, the fluorescence intensity $I'$ of the probe compound is first measured at the first emission wavelength for excitation from a light source at a visible wavelength $\lambda$, and the fluorescence intensity $I''$ is measured for the second emission wavelength after excitation at the same visible wavelength $\lambda$, for example, using the above equipment.

The level of calcium ions in the sample is correlated to and can be determined from the ratio of these two measured emission intensities $I'$ and $I''$ in the same manner discussed beforehand.

The use of the probes as an emission wavelength probe in making ratiometric measurements has the advantage of requiring only a single laser or wavelength excitation source. With STBT, the source could be an Argon Laser at 488 or 514 nm, or even a HeNe laser at 543 nm.

However, the ability to practice this embodiment of the present invention depends on whether the probe displays a fluorescence spectral shift upon binding calcium, which is either a known attribute or can be readily determined for the particular probes of interest within the scope of the invention.

Experimental Procedures

In order perhaps further to illustrate the precepts and utility of the present invention, a description is provided herein of the chemical synthesis and fluorescence spectral characterization of a styryl benzothiazole-containing probe which contains the $Ca^{2+}$ chelating group BAPTA as an integral part of the chromophoric system.

Organic Synthesis

The synthesis of the new class of long-wavelength fluorescent probe compounds is exemplified in the description hereinafter by reference to FIG. 1.

The 5-carboxo-5'-methyl-BAPTA tetramethyl ester 1 was synthesized in five steps generally following a procedure disclosed in the literature (G. Grynkiewicz, M. Poenie and R. Y. Tsien, 1985, *J. Biol. Chem.*, 260,: 3440–3450) with some apparent modifications. The $^1H$ NMR taken was consistent with structure 1.

Then, the hydrolysis of the methyl groups in the 5-carboxo-5'-methyl-BAPTA tetramethyl ester 1 was undertaken because the cyanine/styryl class of dyes is not generally stable under most hydrolytic conditions. Basically, a one hour reflux in 1M NaOH was sufficient to remove the methyl groups, and acidification gave the tetracarboxylic acid-aldehyde 2, i.e., 1-(2-amino-5-carboxophenoxy)-2-(2-amino-5methylphenoxy)ethane-N,N,N',N'-tetraacetic acid, in near quantitative yields. This aldehyde was reacted with N-ethyl-2-methyl-benzothiazolium iodide 3, in EtOH in the presence of small amount of $Et_3N$.

In greater detail, the synthesis protocol was as follows. The 5-carboxo-5'-methyl-BAPTA tetramethyl ester 1 (3.0 g, 8.5 mmol) was suspended in 1N NaOH (aq.) (60 ml). After refluxing the reaction mixture for 1 hour, a clear solution was obtained. This solution was then cooled down in an ice water bath, and concentrated HCl was added dropwise with stirring. The precipitated tetracarboxylic acid-aldehyde 2 was collected by filtration and dried in vacuo to yield a light-yellow powder (2.8 g; 98% yield). The $^1H$ NMR spectrum was ($DMSO-d_6$) $\delta$2.21 (s, 3, Ar'—$CH_3$), 3.99 (s, 4, Ar'—H), 7.41 (m, 2, 2 Ar—H), 9.74 (s, 1, Ar—CHO, 10.60 (bd s, 4, —COOH); MS (FAB), m/e 519 ($M^+$), 541 ($[M-H+Na]^+$), 557 ($[M-2H+Ca]^+$).

To advance to the calcium binding styryl benzothiazole (STBT) probe 4, i.e., 1-(5-(2-(2-ethylbenzothiazoliumyl)ethenyl)-2-aminophenoxy)-2-(2-amino-5-methylphenoxy)ethane-N,N,N',N'-tetraacetic acid, N-Ethyl-2-methyl-benzothiazolium iodide 3 (0.295 g, 1 mmol) was dissolved in ethanol (15 ml). To this solution, the tetracarboxylic acid-aldehyde 2 (0.495 g, 1 mmol) was added, followed by triethylamine (1.5 ml). A bright-red colored dye started to form at reaction temperature (RT), and then the solution was refluxed for 30 minutes to push the reaction to completion. The solvents were then removed in vacuo, and the dark red precipitate was washed with a $CHCl_3$—$Et_2O$ mixture, and dried to yield a fine calcium binding STBT powder 4. The $^1H$ NMR spectrum was consistent with the illustrated structure 4; MS (FAB), m/e 646 ($M^+$), 738 ($[M+4Na]^+$).

Absorbance and Fluorescence Properties

Fluorescence emission spectra (uncorrected) were then obtained for this probe compound on a SLM 8000 fluorometer using a Hammamatsu R928 photomultiplier tube. Excitation spectra were corrected using Rhodamine B in propylene glycol as a quantum counter with ratiometric dual-channel recording. Quantum yields were determined relative to Rhodamine 6G ($\Phi_F=0.95$ in MeOH). Fluorescence lifetimes and/or intensity decays were determined using the frequency-domain method (E. Gratton and M. Limkeman, 1983, *Biophys. J.*, 44: 315–324, J. R. Lakowicz and B. P. Maliwal, 1985, *Biophys. Chem.*, 21: 61–78 and G. Laczko, I. Gryczynski, W. Wiczk, H. Malak and J. R. Lakowicz, 1990, *Rev. Sci. Instrum.*, 61: 2331–2337). These disclosures are expressly incorporated herein by reference.

Calibrated buffers with known concentrations of $Ca^{2+}$ were obtained, for example, using a calcium calibration kit (two aqueous solutions buffered with 10 mM MOPS at pH 7.2, containing 100 mM KCL and either 10 mM EGTA or 10 mM CaEGTA, obtained from Molecular Probes. $^1H$ NMR spectra at 300 MHz were obtained using a GE-300 instrument. Mass spectral measurements were carried out at the Middle Atlantic Mass Spectroscopy Facility at the John Hopkins University, an NSF Shared Intrumentation Facility.

Results

Figure 2:
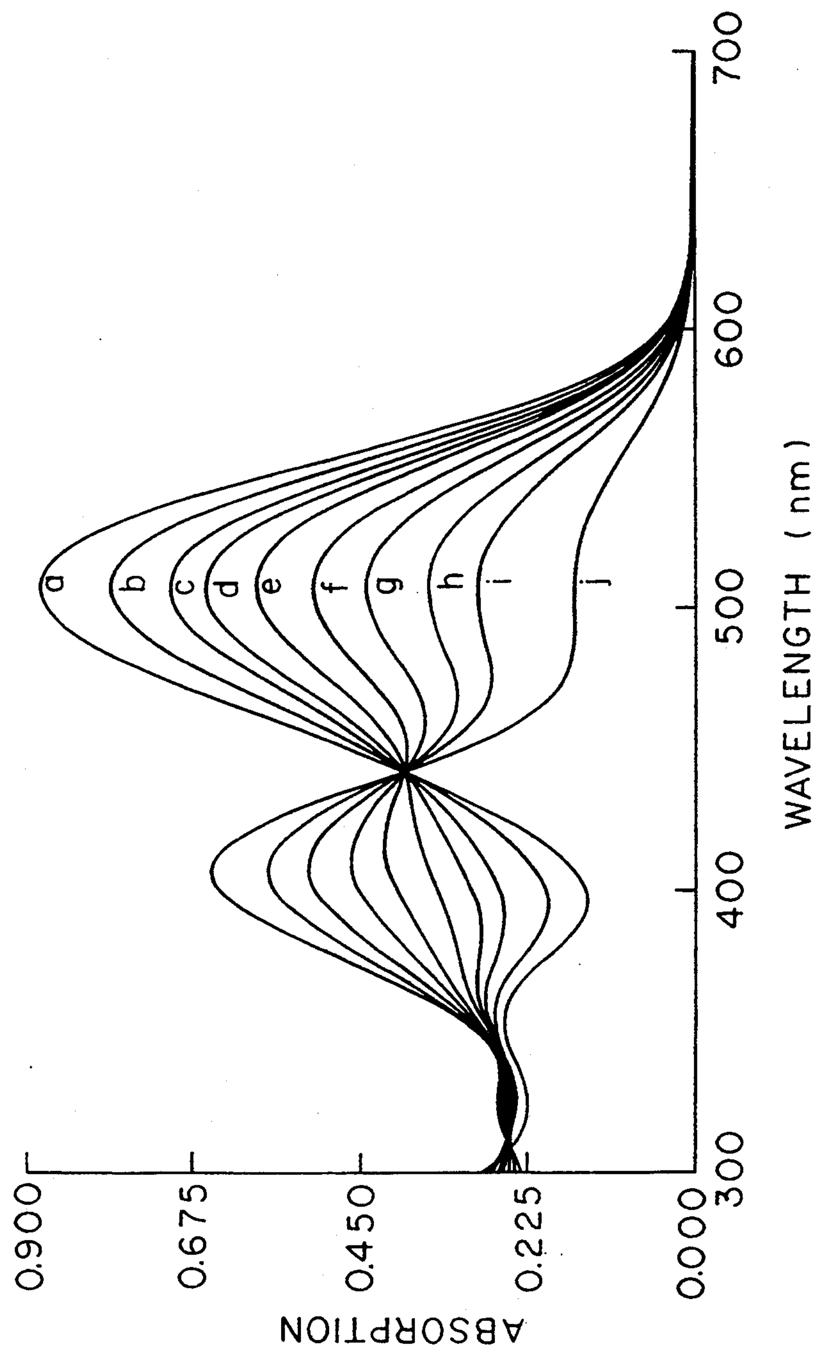
FIG. 2 shows absorption spectra of the STBT $Ca^{2+}$ probe compound as a function of the following $Ca^{2+}$ concentrations (a 0, (b 0.45, (c 1.06, (d 1.46, (e 2.01 (f 2.72, (g 3.67, (h 4.95, (i 6.65, (j 38 μm $Ca^{2+}$.

As shown in FIG. 2, the absorption spectra of the STBT probe displays a dramatic shift in the presence of $Ca^{2+}$. In the absence of $Ca^{2+}$ the absorption spectra displays a maximum near 508 nm. Addition of saturating amounts of $Ca^{2+}$ results in a dramatic shift of the absorption band centered at 407 nm, with the absorption at 508 nm being decreased by about 80%. The absorption spectra at varying amounts of $Ca^{2+}$ show a clear isosbestic point at 440 nm. These dramatic $Ca^{2+}$-dependent shifts in the STBT absorption spectra provide ample opportunities for exitation wavelength ratiometric measurements of $Ca^{2+}$.

Importantly, the STBT probe can be excited with a range of simple and currently available laser sources ranging from the HeCd lines at 325, 442 nm, as well as the newly available HeCd line at 354 nm. The STBT probe can also be excited with several Argon ion laser lines at 364, 488 and 514 nm. And finally, excitation could even be accomplished with a green HeNe line at 543 nm. Multi-line lasers with a filter wheel, tunable acousto-optic filter or other known rapid wavelength selection device also can be used to provide ratiometric $Ca^{2+}$ imaging in the present invention.

The visible absorption bands of STBT will facilitate confocal microscopy. In contrast, aberration corrected optics in the UV region of the spectrum are required for known $Ca^{2+}$ probes such as Fura-2 and Quin-2. Such optics are scarce and expensive, and the use of visible wavelengths in the present invention circumvents this problem.

Figure 3:
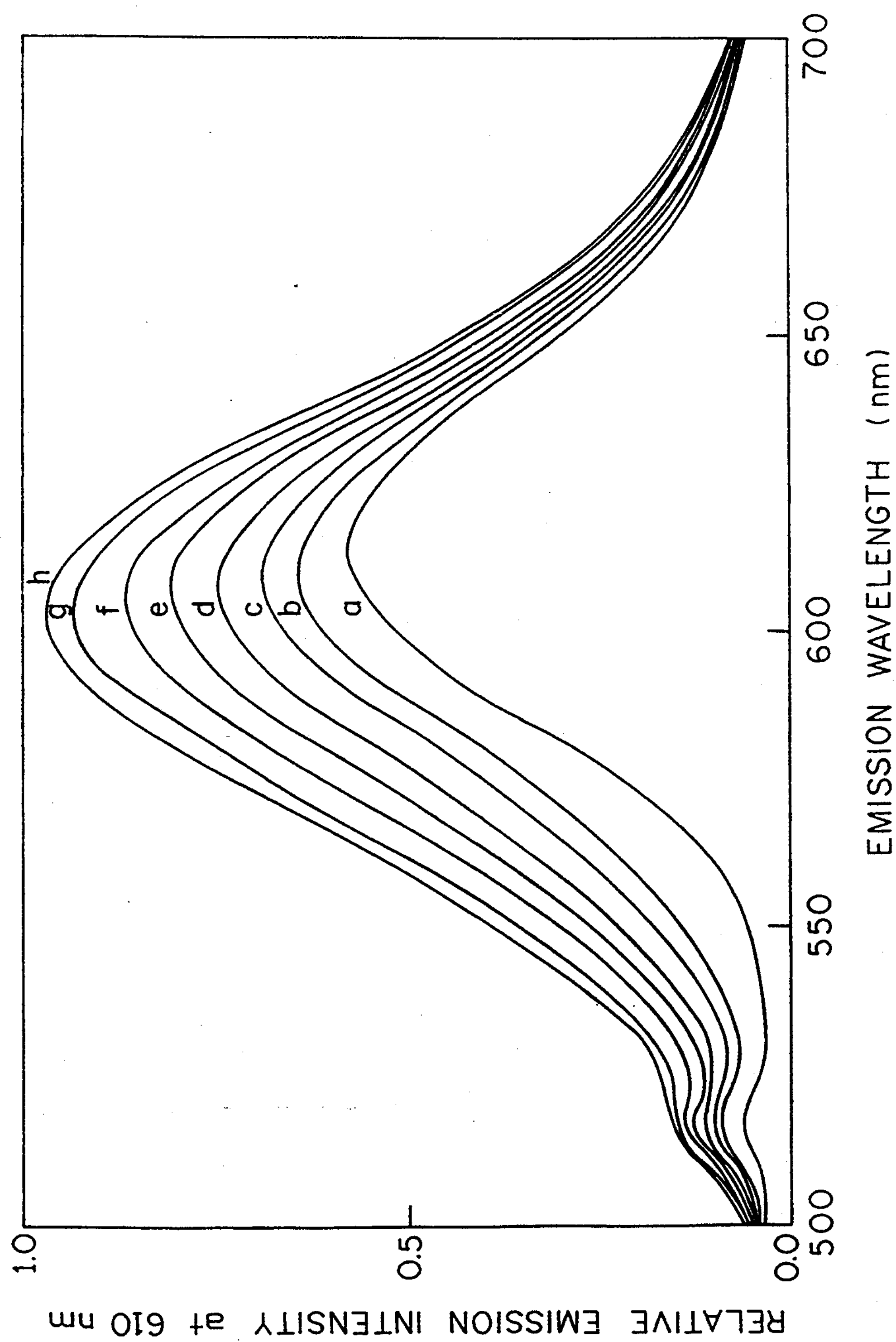
FIG. 3 shows emission spectra of the STBT $Ca^{2+}$ probe compound as a function of the following $Ca^{2+}$ concentrations, excitation is at the isosbestic point, (440 nm), (a 0, (b 1.06, (c 1.46, (d 2.01 (e 2.72, (f 3.67, (g 4.95, (h 38 μm $Ca^{2+}$.

Calcium-dependent emission spectra of STBT are shown in FIG. 3 with excitation performed at the isosbestic wavelength of 440 nm. The emission displays a modest blue shift from 613 to 603 nm in the presence of increasing amounts of $Ca^{2+}$. There is also a 65% $Ca^{2+}$-dependent increase in intensity. This combination of spectral shift with an intensity change is considered to be adequate to allow emission wavelength-ratiometric measurements of $Ca^{2+}$.

While the change in the emission spectrum upon complexation with $Ca^{2+}$ may appear small, the changes, nonetheless, are considerably larger than the known wavelength-ratiometric sodium and potassium probes (SBFI, PBFI), for example, see A. Minta and R. Y. Tsien, (1989), *J. Biol. Chem.*, 264, 19449–19457.

Figure 4:
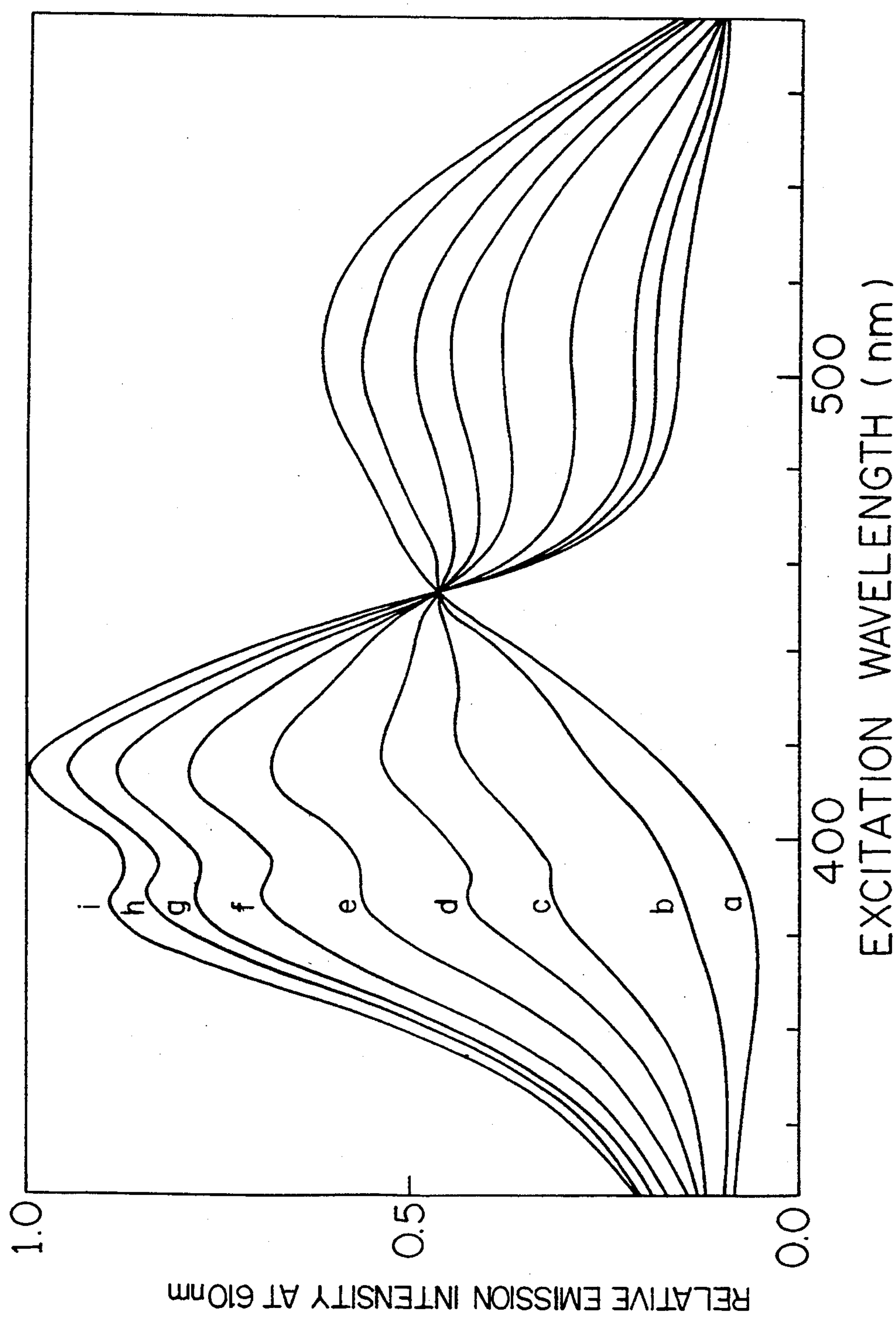
FIG. 4 shows corrected excitation spectra of STBT probe as a function of the following $Ca^{2+}$ concentrations (Emission at 610 nm), (a 0, (b 0.45, (c 1.06, (d 1.46, (e 2.01 (f 2.72, (g 3.67, (h 4.95, (i 6.65, (j 38 μm $Ca^{2+}$.

Further, calcium-dependent "corrected" excitation spectra of STBT are shown in FIG. 4. The spectra generally mimic the absorption spectra in FIG. 2, but some residual structure is seen at 380–400 nm which is considered as due to the spectral lines of the xenon lamp used in the spectrofluorometer.

A comparision of FIG. 4 (excitation spectra) and FIG. 2 (absorption spectra) indicates that for excitation at 508 nm that the $Ca^{2+}$-dependent decrease in intensity is 5-fold, whereas the $Ca^{2+}$-dependent decrease in absorbance is 8-fold. This difference is considered to be attributable to the higher quantum yield of the $Ca^{2+}$-bound form. Conversely, for excitation at 407 nm the $Ca^{2+}$-dependent increase in the emission intensity is 14-fold, whereas the $Ca^{2+}$-dependent increase in absorption is 4-fold. This difference is considered to be due to the combined larger absorbance and quantum yield of the $Ca^{2+}$-bound form.

Figure 5:
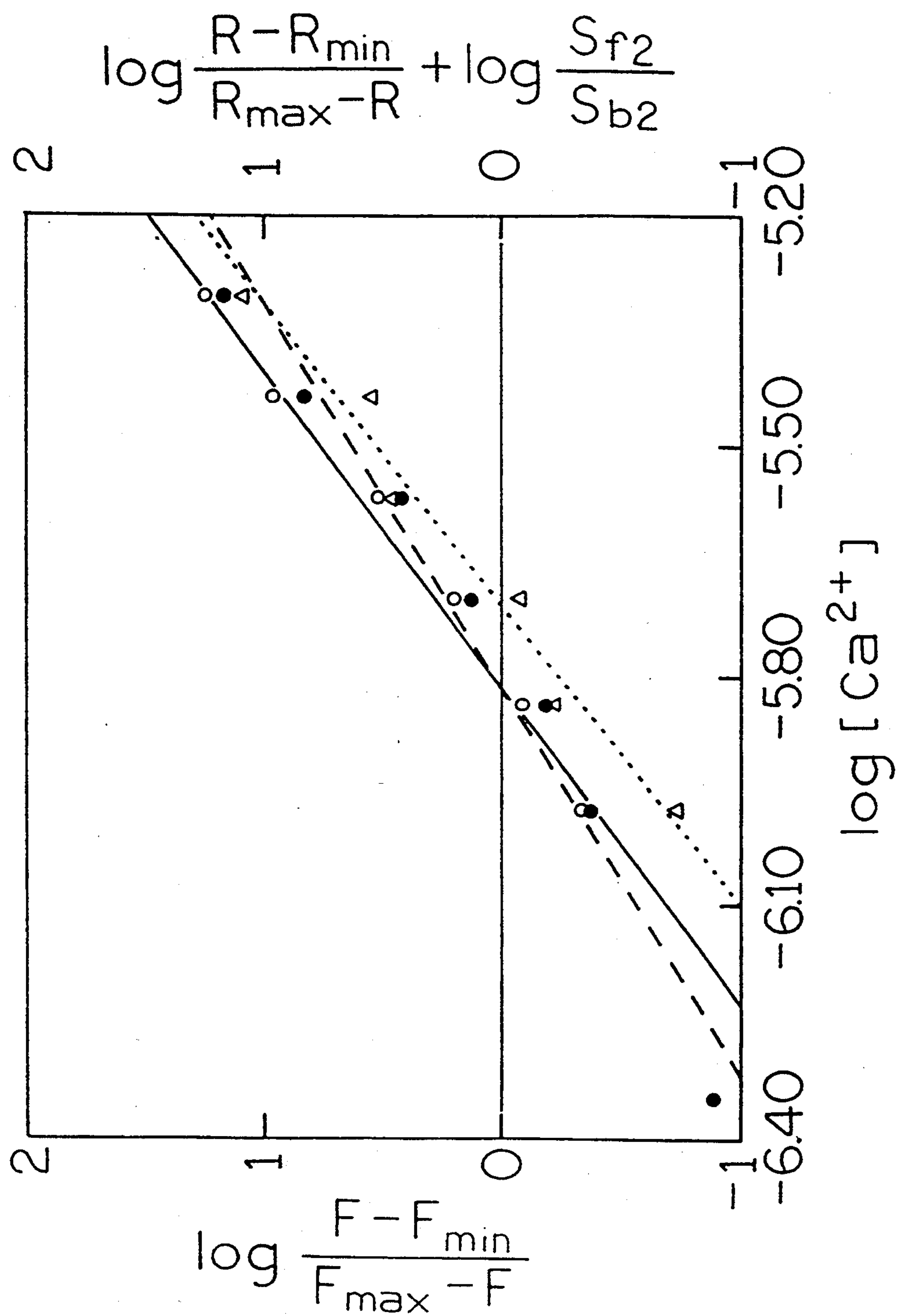
FIG. 5 shows $K_d$ determination by Hill and modified Hill plots (∘ and Δ): wherein fluorescence data were obtained from excitation spectra, (emission intensity at 610 nm for 415 nm excitation). The closed circles (( )) represent ratios calculated from excitation spectrum data, for $\lambda_1=407$ nm and $\lambda_2=508$ nm. The open triangles (Δ) represent ratios calculated from emission spectrum data, for $\lambda_1=590$ nm and $\lambda_2=615$ nm.

The $Ca^{2+}$ dependent excitation and emission spectra allows determination of the dissociation constant of STBT for $Ca^{2+}$. The plot of $\log\{(F-F_{min})/(-F_{max}-F)\}$, obtained from the excitation spectra in FIG. 4, versus $\log(Ca^{2+})$ yields $\log(K_d)$ as the x-intercept, as shown in FIG. 5 (open circles). The dissociation constant $K_d$ can also be determined using the ratio of fluorescence intensities at 610 nm, excited at 407 and 508 nm (closed circles). Both plots (open and closed circles) yielded the same dissociation contant for STBT and $Ca^{2+}$, 1.5 μM. Alternatively, such a plot can be constructed using the isosbestic point as one of the two excitation wavelengths. Importantly, ratiometric $Ca^{2+}$ measurements can also be obtained using a single excitation wavelength of 440 nm, and two emission wavelengths of 590 and 615 nm (FIG. 5, open triangles).

The $Ca^{2+}$ dependent absorption spectra allow determination of the dissociation constant of the STBT probe for $Ca^{2+}$, which constant is larger than that known for Fura-2 near 150 nm, e.g., see G. Grynkiewicz, M. Poenie and R. Y. Tsien, *J. Biol. Chem.*, 260, 3440–3450, and for probes with higher dissociation constants, such as Calcium Green-5N, Mag-fura-2 and Mag-fura-5 that have become of interest for studies of $Ca^{2+}$ transients in cells, as discussed in K. Kuba et al, *J. Theor. Biol.*, 1981, 93: 1009; A. Goldpeter et al, *Proc. Natl. Acad. Sci.*, 87, 1461 (1990).

The presence of an absorption spectral shift enables wavelength-ratiometric imaging of $Ca^{2+}$ using visible wavelengths. Wavelength-ratiometric measurements in the present invention are possible using a wide range of wavelengths from 350 nm to 580 nm, thereby allowing the use of multi-line lasers, as well as the more common filter wheels or rotating mirror monochromators.

The present invention also contemplates further refinement of spectral properties of calcium-binding STBT. That is, STBT displays features of a short fluorescence lifetime near 100 ps in the presence of $Ca^{2+}$ and near 70 ps in the absence of $Ca^{2+}$ and a low quantum yield in aqueous solution. These features are believed to be attributable to possible rotation around the ethylenic carbon bond during the lifetime of the excited state.

In view of the above data results, the inventors envisage a variety of STBT probe derivatives which can be useful in cellular $Ca^{2+}$ imaging. For instance, membrane-permeable forms of STBT could readily be prepared by known routes. Further, it is postulated that the quantum yield and/or lifetime of the probe compound could be increased by the addition of binding groups to prevent rotation about the ethylenic binds.

While the invention has been described in detail and with reference to specific embodiments, it will be apparent to one skilled in the art that various changes and modifications can be made in these embodiments without departing from the spirit and scope of the invention as defined by the following claims.

We claim:

1. A fluorescent calcium-binding compound for making wavelength-ratiometric or intensity-ratiometric measurements of calcium ion concentrations having the formula:

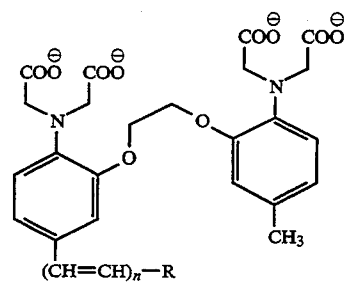

where n represents an integer of 1, 2 or 3 and R represents thiaflavin or

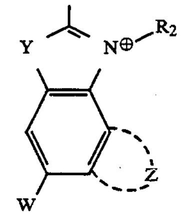

wherein $R_2$ is selected from the group consisting of methyl, ethyl, sulfopropyl, sulfobutyl, and carboxymethyl, Y is selected from the group consisting of S, $(CH_3)_2C$, and O; W is selected from the group consisting of H, Cl, and $OCH_3$; and Z is an optional fused aromatic ring.

2. The fluorescent calcium-binding compound of claim 1, wherein R is selected from the group consisting of benzothiazole, napthothiazole, thiaflavin, indolenine, chloroindolenine, methoxybenzothiazole, and methoxyindolenine.

3. A fluorescent calcium-binding compound for making wavelength-ratiometric or intensity-ratiometric measurements of calcium ion concentrations having the formula:

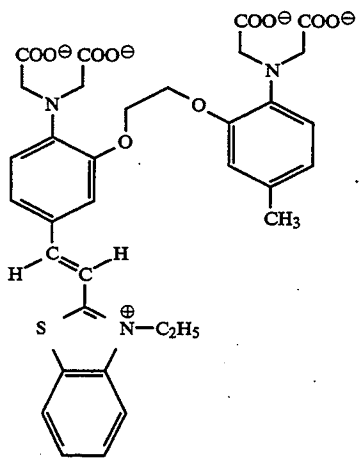

4. A method of making wavelength-ratiometric or intensity-ratiometric measurements of calcium concentration in a sample containing calcium ions using a wavelength of about 400 nm or more, comprising contacting a sample containing calcium ions with a probe compound of the following formula in sufficient quantity to act as a fluorescent optical indicator independent of concentration of said probe compound:

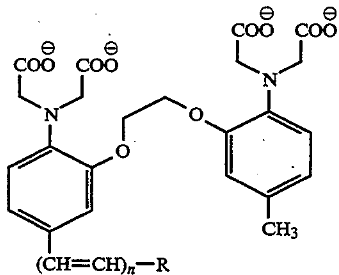

wherein n represents an integer of 1, 2 or 3 and R represents thiaflavin or

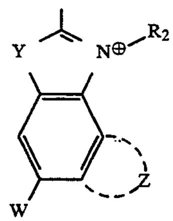

wherein $R_2$ is selected from the group consisting of methyl, ethyl, sulfopropyl, sulfobutyl, and carboxymethyl, Y is selected from the group consisting of S, $(CH_3)_2C$, and O; W is selected from the group consisting of H, Cl, and $OCH_3$; and Z is an optional fused aromatic ring; and measuring the calcium concentration in the sample by wavelength-ratiometry or intensity-ratiometry using a wavelength of about 400 nm or more.

5. The method of claim 4, wherein R is selected from the group consisting of benzothiazole, napthothiazole, thiaflavin, indolenine, chloroindolenine, methoxybenzothiazole, and methoxyindolenine.

6. The method of claim 4, wherein said sample contains biological tissues.

7. The method of claim 4, wherein said measuring is effected by flow cytometry and is used to measure intracellular calcium concentration.

8. The method of claim 4, wherein said measuring comprises forming two or three-dimensional calcium concentration images in fluorescence microscopy.

9. The method of claim 4, wherein said measuring comprises the following steps:

(1) illuminating said sample with a light source at a first excitation visible wavelength $\lambda_1$ and measuring the resulting fluorescence intensity $I_1$ radiated from the sample, then (2) illuminating said sample with a light source at a second excitation visible wavelength $\lambda_2$ and measuring the resulting fluorescence intensity $I_2$, wherein $\lambda_1$ and $\lambda_2$ are different, and (3) converting the fluorescence intensities $I_1$ and $I_2$ into electrical signals, determining a ratio therefrom, and determining the concentration of calcium in said sample with said ratio.

10. The method of claim 4, wherein said measuring comprises the following steps:

(1) illuminating said sample containing calcium ions with a light source at a excitation visible wavelength $\lambda$ and measuring the resulting fluorescence intensity $I'$ at emission wavelength $\lambda'$, (2) illuminating said sample containing calcium ions with a light source also at excitation wavelength $\lambda$ and measuring the resulting fluorescence intensity $I''$ at emission wavelength $\lambda''$, wherein $\lambda'$ and $\lambda''$ are different, and (3) converting the fluorescence intensities $I'$ at $\lambda'$ and $I''$ at $\lambda''$ into electrical signals, determining a ratio therefrom, and determining the concentration of calcium in said sample containing calcium ions with said ratio.

11. The method of claim 9, wherein said excitation visible wavelengths $\lambda_1$ and $\lambda_2$ are each greater than about 400 nm.

12. The method of claim 9, wherein said excitation visible wavelengths $\lambda_1$ and $\lambda_2$ are each selected from a range of about 400 nm to about 670 nm.

13. A method of making wavelength-ratiometric or intensity-ratiometric measurements of calcium concentration in a sample containing calcium ions using a wavelength of about 400 nm or more, comprising contacting a sample containing calcium ions with a probe compound of the following structure in sufficient quantity to act as a fluorescent indicator independent of concentration of said probe compound:

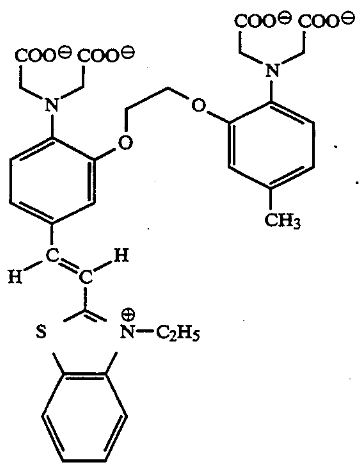

and measuring the calcium concentration in the sample by wavelength-ratiometry or intensity-ratiometry using a wavelength of about 400 nm or more.

14. The method of claim 13, wherein said measuring comprises the following steps:

(1) illuminating said sample with a light source at a first excitation visible wavelength $\lambda_1$ and measuring the resulting fluorescence intensity $I_1$ radiated from the sample, then (2) illuminating said sample with a light source at a second excitation visible wavelength $\lambda_2$ and measuring the resulting fluorescence intensity $I_2$, wherein $\lambda_1$ and $\lambda_2$ are different, and (3) converting the fluorescence intensities $I_1$ and $I_2$ into electrical signals, determining a ratio therefrom, and determining the concentration of calcium in said sample with said ratio.

15. The method of claim 13, wherein said measuring comprises the following steps:

(1) illuminating said sample containing calcium ions with a light source at a excitation visible wavelength $\lambda$ and measuring the resulting fluorescence intensity $I'$ at emission wavelength $\lambda'$, (2) illuminating said sample containing calcium ions with a light source also at excitation wavelength $\lambda$ and measuring the resulting fluorescence intensity $I''$ at emission wavelength $\lambda''$, wherein $\lambda'$ and $\lambda''$ are different, and (3) converting the fluorescence intensities $I'$ at $\lambda'$ and $I''$ at $\lambda''$ into electrical signals, determining a ratio therefrom, and determining the concentration of calcium in said sample containing calcium ions with said ratio.

16. The method of claim 14, wherein said excitation visible wavelengths $\lambda_1$ and $\lambda_2$ are each greater than about 400 nm.

17. The method of claim 14, wherein said excitation visible wavelengths $\lambda_1$ and $\lambda_2$ are each selected from a range of about 400 nm to about 670 nm.

18. The method of claim 15, wherein said emission wavelengths $\lambda'$ and $\lambda''$ are each greater than 500 nm.

* * * * *